United States Patent [19]

Katsumata et al.

[11] Patent Number: 5,153,120
[45] Date of Patent: Oct. 6, 1992

[54] PROCESS FOR THE PRODUCTION OF γ-GLUTAMYL TRANSPEPTIDASE

[75] Inventors: Ryoichi Katsumata, Machida, Japan; Toru Mizukami, New York, N.Y.; Shigenori Ohta, Komae; Moriyuki Sato, Machida; Kazuo Yamaguchi, Sagamihara, all of

[73] Assignee: Kyowa Hakko Kogyo Co., Ltd., Tokyo, Japan

[21] Appl. No.: 652,151

[22] Filed: Feb. 7, 1991

[30] Foreign Application Priority Data

Feb. 7, 1990 [JP] Japan .................................. 2-27740

[51] Int. Cl.$^5$ ........................ C12P 21.02; C12N 1/21; C12N 15/54; C07H 21/00
[52] U.S. Cl. .............................. 435/60.1; 435/252.3; 435/320.1; 435/193; 435/832; 536/27
[58] Field of Search ................. 435/193, 320.1, 252.3, 435/832, 69.1, 71.2, 252.31

[56] References Cited

U.S. PATENT DOCUMENTS 4,990,444 2/1991 Aretz et al. ........................... 435/15

FOREIGN PATENT DOCUMENTS

27323/88 6/1989 Australia .

OTHER PUBLICATIONS

Suzuki et al., 1989, J. Bacteriology 171(9)5169–5172.
Rajpert-De Meyts et al., 1988, Proc. Natl. Acad. Sci. USA 85:8840–8844.
Meister and Tate, Ann. Rev. Biochem., 45:559–604, 1976.
Nakayama et al, J. Bacteriol., 160:341–346, 1984.
Suzuki et al., J. Bacteriol., 168:1325–1331, 1986.
Suzuki et al., Biochem. Biophys. Res. Commun., 150:33–38, 1988.
Hara and Ueda, Fermentation and Industry, 43:910, 1985.
Asada et al., Summary of Lelctures at 1989 General Meeting of Japan Society for Bioscience, Biotechnology and Agrochemistry, 125.
Williams and Throne, J. Bio. Chem., 210:203–217, 1954.
Williams et al., J. Bacteriol., 146(3):1162–1165, 1981.
Ito et al., Nucelic Acid Res., 10(5):1755–1769, 1982.
Saito and Miura, Biochim. Biophys. Acta. 72:619–629, 1963.
Spizizen et al., Ann. Rev. Microbiol. 20:371–400, 1966.
Akamatsu and Sekiguchi, Agric. Biol. Chem., 46:1617–1621, 1982.
Gryczan and Dubnau, Proc. Natl. Acad. Sci. USA, 75:1428, 1978.
Contente and Dubnau, Plasmid 2:555–571, 1979.
Gryczan et al., J. Baceriol., 134:318–329, 1978.
Rigby et al., J. Mol. Biol. 113:237–251, 1977.
Gryczan et al., J. Bacteriol., 141:246–253, 1980.
Messing, Methods in Ezymology, 101:20–78, 1983.
Vieira and Messing, Methods in Ezymology, 153:3–11, 1987.
Henikoff, Gene, 28:351–359, 1984.
Yanisch-Perron et al., Gene 33:103–119, 1985.
Yamane, Nippon Nogeikagakukai-shi, 61:64–67, 1987.
McKenzie et al., Plasmid, 15:93–103, 1986.
Japanese Patent Application LOP Publn. No. 1985-2, 135.
Japanese Patent Application LOP Publn. No. 1988-181, 996.
Debabov, The Molecular Biology of the Bacilli, 1, 331, Academic Press, 1982.

Primary Examiner—Robert A. Wax
Assistant Examiner—G. E. Bugaisky
Attorney, Agent, or Firm—Pennie & Edmonds

[57] ABSTRACT

The present invention provides a recombinant DNA comprised of a vector DNA and a DNA fragment containing a gene coding for γ-glutamyl transpeptidase derived from Bacillus subtilis. The invention also provides a process for producing γ-glutamyl transpeptidase, which comprises culturing in a culture medium a microorganism belonging to the genus Bacillus which is carrying recombinant DNA comprised of a vector DNA and DNA fragment which contains a gene coding for γ-glutamyl transpeptidase derived from the genus Bacillus, accumulating γ-glutamyl transpeptidase in the culture, and recovering γ-glutamyl transpeptidase therefrom.

7 Claims, 3 Drawing Sheets

Restriction Map of Cloned fragment in pG31

PROCESS FOR THE PRODUCTION OF γ-GLUTAMYL TRANSPEPTIDASE

FIELD OF THE INVENTION

This invention relates to a process for the production of γ-glutamyl transpeptidase (EC 2.3.2.2).

γ-glutamyl transpeptidase is an enzyme which catalyzes (1) hydrolysis of glutathione to produce glutamic acid or (2) the transfer of the γ-glutamyl group of glutathione to an amino acid or peptide, as follows:

(1) Hydrolysis:

(2) Transfer:

(wherein A is an amino acid or a peptide)

γ-Glutamyl transpeptidase is useful as a dough conditioner for increasing specific volume, for improving content, and for suppression of retrogradation of bread [Japanese Patent Application LOP Publn. No. 1985-2,135].

PRIOR ART

γ-glutamyl transpeptidase is present in various organisms from bacteria to higher animals [A. Meister and S. Tate: Ann. Rev. Biochem., 45, 559 (1976)]. This enzyme has been isolated and purified most often from the organs of higher animals. The production and purification of γ-glutamyl transpeptidase from bacteria has been studied in *Proteus mirabilis* and *Escherichia coli* [H. Kumagai et al., J. Bacteriol., 160, 341 (1984) and H. Suzuki et al., J. Bacteriol., 168, 1325 (1986)]. Also, the cloning of a γ-glutamyl transpeptidase gene derived from *Escherichia coli* has been reported (H. Suzuki et al., Biochem. Biophys. Res. Commun., 150, 33 (1988)]. The use of γ-glutamyl transpeptidase, derived from bacteria, as an additive for food is undesirable from a safety standpoint. It has been reported that *Bacillus natto* [Debabov. V. G., "The Molecular Biology of the Bacilli," 1, 331, Academic Press (1982)] and *Bacillus licheniformis*, produce a γ-glutamyl transpeptidase that is non-toxic. [Hara and Ueda: "Fermentation and Industry, 43, 910 (1985) and Asada et al., Summary of Lectures at 1989 General Meeting of Japan Society for Bioscience, Biotechnology and Agrochemistry p.125]. It has also been reported that *Bacillus subtilis*, a very closely related strain to *Bacillus natto*, produces an enzyme having γ-glutamyl transferase activity [W. Williams and C. B. Throne, J. Biol. Chem., 210, 203 (1954)]. However, the yield of the enzyme from the genus Bacillus is poor and unsuitable for large quantity production of the enzyme.

The method of producing γ-glutamyl transpeptidase by cell culture of Pseudomonas, Proteus, Arthrobacter and *Bacillus subtilis* has been disclosed [Japanese Patent Application LOP - Publn. No. 1988-181, 996]. However, the yield is low and the bacteria, except for *Bacillus subtilis* do not produce a suitable enzyme for use in food from a safety standpoint. Furthermore, the above mentioned microorganisms are unsuitable for industrial production since further purification is needed to remove contaminating proteins due to cell degradation and cellular debris.

PROBLEMS TO BE SOLVED BY THE INVENTION

One objective of the invention is to provide a bacterial strain capable of producing γ-glutamyl transpeptidase in high yield and without toxic contaminants. This would make the enzyme useful as a dough conditioner. Another objective of the invention is to provide a method for inexpensive and simple production of the enzyme using said bacterial strain.

MEANS FOR SOLVING THE PROBLEMS

In the field of molecular biology, genetically engineered bacteria are often used for producing many useful proteins and enzymes. The bacterium containing a gene encoding for a particular protein or enzyme is cultured to express the gene product. When genetic engineering is utilized for such production, it is essential to select a suitable, safe host bacterium as well as a simple, efficient method of purifying the protein produced. The genus Bacillus is useful for secreting large amounts of protein from the cell and *Bacillus subtilis*, a closely related strain to *Bacillus natto*, is one of the safest, non-pathogenic species.

The inventors have screened a number of strains belonging to *Bacillus subtilis* in order to find a strain capable of producing and secreting γ-glutamyl transpeptidase and found *Bacillus subtilis* SJ138 to be such a γ-glutamyl transpeptidase-producing strain. Since the SJ138 strain has poor γ-glutamyl transpeptidase-producing ability, we have attempted to improve the productivity thereof. We have cloned the gene of γ-glutamyl transpeptidase from the strain, self-cloned it into a plasmid vector of *Bacillus subtilis*, plasmid pUB110, or a derivative thereof, to construct a recombinant plasmid. A bacterium of the genus Bacillus, such as γ-glutamyl transpeptidase-producing strain SJ138, or a non-γ-glutamyl transpeptidase producing strain *Bacillus subtilis* Marburg BR151 [ATCC 33677, D. M. Williams et al., J. Bacteriol., 146, 1162 (1981)] can be transformed with the recombinant plasmid. The transformant of the SJ138 host now contains multiple copies of the gene and produces a higher yield of the enzyme than the original strain SJ138.

SUMMARY OF THE INVENTION

The present invention provides a process for producing γ-glutamyl transpeptidase, which comprises culturing in a culture medium a microorganism belonging to the genus Bacillus which is carrying a recombinant DNA comprised of a vector DNA and a DNA fragment which contains a gene coding for γ-glutamyl transpeptidase derived from the genus Bacillus, accumulating the γ-glutamyl transpeptidase in the culture, and recovering the γ-glutamyl transpeptidase.

The invention further provides a gene which codes for γ-glutamyl transpeptidase and has the nucleotide sequence as defined in the Sequence Listing by SEQ ID: No. 1.

The invention further provides a recombinant DNA comprised of vector DNA and a DNA fragment containing a gene coding for γ-glutamyl transpeptidase which is obtained from *Bacillus subtilis*.

The invention further provides a microorganism belonging to the genus Bacillus and carrying a recombinant DNA comprised of a vector DNA and a DNA fragment containing a gene coding for γ-glutamyl transpeptidase which is obtained from *Bacillus subtilis*.

In the Figures: E is EcoRI, X is XbaI, B is BamHI, S is SphI, B/Sa is a BamHI/Sau3A ligation site, Sc is SacI, K is KonI, Sm is SmaI, Sl is SalI, P is PstI, H is HindIII, N/Sm is a NruI/SmaI ligation site, C is ClaI, Hc is HincII, Km is Kanamycin-resistant marker, Cm is Chloramphericol-resistant marker, and Ap is an Ampicillin resistant marker.

DETAILED DESCRIPTION OF THE INVENTION

Both the DNA fragment containing the gene encoding γ-glutamyl transpeptidase and the plasmid vector are derived from the genus Bacillus. The gene for γ-glutamyl transpeptidase is found in chromosomal DNA. The gene is inserted into the vector, using conventional recombinant DNA technology, and is duplicated in the genus Bacillus.

Examples of bacteria which can produce and secrete γ-glutamyl transpeptidase are *Bacillus subtilis* SJ138 (FERM BP-2694), *Bacillus subtilis* ATCC9372, and *Bacillus brevis* ATCC 10027. These strains were selected from various Bacillus strains by measuring γ-glutamyl transpeptidase activity in the supernatant of their culture. The γ-glutamyl transpeptidase activity can be determined using γ-glytamyl-p-nitroanilide as a substrate and measuring the amount of p-nitroaniline produced by the enzyme reaction using a colorimeter at 410 nm.

The cloning of the γ-glutamyl transpeptidase gene derived from *Bacillus subtilis* SJ138 is described below as an illustrative example. *Bacillus subtilis* SJ138 was deposited with the Fermentation Research Institute Agency of Industrial Science and Technology on Dec. 2, 1989, under the Budapest Treaty and assigned the accession number FERM BP-2694.

The steps used to clone the γ-glutamyl transpeptidase gene of *Bacillus subtilis* SJ138 are as follows:

(a) Isolation and purification of the γ-glutamyl transpeptidase, (b) Determination of the amino acid sequence of the γ-glutamyl transpeptidase, (c) Synthesis of a DNA probe corresponding to the amino acid sequence, (d) Detection of the γ-glutamyl transpeptidase gene on chromosomal DNA of SJ138, using the probe, and (e) Cloning of the gene into a suitable vector.

(1) Isolation and purification of the γ-glutamyl transpeptidase

The γ-glutamyl transpeptidase can be purified by the standard methods. γ-Glutamyl transpeptidase may be purified from the supernatant of a culture by fractional precipitation using neutral salts, organic solvents, etc., or by ion exchange chromatography. The fractions eluted from the column are tested for γ-glutamyl transpeptidase activity and the active fractions are collected. For example, γ-glutamyl transpeptidase may be purified from the supernatant of a culture by ethanol precipitation, lyophilization, DEAE-cellulose column chromatography and hydroxyapatite column chromatography. Determination of the molecular weight of the purified γ-glutamyl transpeptidase from SJ138 by gel filtration and SDS-polyacrylamide gel electrophoresis suggests that the enzyme is a dimer consisting of about a 41 KDa (kilo dalton) subunit and a 23 KDa subunit (1:1).

(2) Determination of the amino acid sequence of γ-glutamyl transpeptidase

The purified γ-glutamyl transpeptidase enzyme is separated into two subunits using reverse high pressure liquid chromatography. Each of the subunits is fragmented using a protease, for example trypsin, and the fragments are fractionated by high pressure liquid chromatography. The amino acid sequences of the peptide fragments are analyzed by the standard method of using an amino acid sequencer.

(3) Synthesis of an oligonucleotide probe corresponding to the amino acid sequence of γ-glutamyl transpeptidase Oligonucleotides, of about 15-18 bases long corresponding to the 5-6 amino acid sequence of the enzyme, are synthesized. The oligonucleotides are used as a probe for colony hybridization. Since codons 1-6 correspond to a single amino acid, several oligonucleotides are prepared for the probe. When creating a probe, it is desirable to select a region of the amino acid sequence where fewer oligonucleotides are needed to correspond. One of the preferable probes, corresponding to the sequence of amino acids 5-10 of the partial sequence, as defined in the Sequence Listing by SEQ ID No. 3, of the 41 KDa subunit, is a mixture of 32 types of the 17 bp oligonucleotide as defined in the Sequence Listing by SEQ ID No. 4, (where N is A, T, G or C, Y is T or C, and R is A or G) (designated as probe L). Another preferable probe includes a mixture of 64 types of the 17 bp oligonucleotide as defined in the Sequence Listing by SEQ ID No. 7, designated as probes complementary to the oligonucleotide as defined in the Sequence Listing of SEQ ID No. 6 encoding the amino acids 2-7 of the partial sequence, as defined in the Sequence Listing by SEQ ID 5, of the 23 KDa subunit.

These oligonucleotides may be synthesized using a commercially available DNA synthesizer or by the solid phase phosphotriester method [H. Ito et al., Nucleic Acids Res., 10, 1755 (1982)]. The resultant oligonucleotides may be purified by high pressure liquid chromatography.

(4) Southern hybridization of the γ-glutamyl transpeptidase gene from the chromosome of SJ138 using the synthesized DNA probe Southern hybridization [E. M. Southern, J. Mol. Biol., 98, 103 (1975)] is carried out to detect the γ-glutamyl transpeptidase gene on the chromosome of SJ138 using the synthetic oligonucleotide probe described above. The sequences encoding the two subunits in the SJ138 chromosome may hybridize with the probe. The chromosomal DNA of SJ138 is digested with an appropriate restriction enzyme and fractionated by agarose gel electrophoresis. The DNA fragments are blotted onto a nitrocellulose filter, fixed, and then hybridized with the labelled probe.

The chromosomal DNA of SJ138 may be prepared from the culture according to the method of H. Saito and K. Miura [Biochim. Biophys. Acta 72 619 (1963)]. Digestion of the chromosomal DNA with a restriction enzyme and agarose gel electrophoresis may be carried out according to standard methods [T. Maniatis et al.. Molecular Cloning, Cold Spring Harbor Laboratory (1982)].

We have found that both the probe L derived from the 41 KDa subunit and the probe S derived from the 23 KDa subunit hybridized with a 2.8 Kb HindIII fragment and a 2.9 Kb EcoRI fragment in close proximity to each other. These results suggest that the sequences encoding the two subunits are located in close proximity to each other on the SJ138 chromosome.

(5) Cloning the γ-glutamyl transpeptidase gene using a *Bacillus subtilis* host-vector system In the "shot gun" approach, the chromosomal DNA containing the γ-glutamyl transpeptidase gene and a plasmid vector derived from the genus Bacillus are digested with an appropriate restriction enzyme. Then, the resultant fragments are ligated. The construct may then be used to transform the competent cells of *Bacillus subtilis* Marburg or protoplast of *Bacillus subtilis* [J. Spizizen et al., Ann. Rev. Microbiol., 20, 371 (1966): T. Akamatsu and J. Sekiguchi, Agric. Biol. Chem., 46, 1617 (1982)]. The transformants are screened for γ-glutamyl transpeptidase activity. A nitrocellulose filter is placed on agar and the transformants are plated on the filter. After colonies have formed, the colonies are transferred to the filter soaked with γ-glutamyl p-nitroaniline, the substrate of γ-glutamyl transpeptidase. The enzyme-substrate reaction produces p-nitroaniline, a yellow substance. The transformants that show yellow around a colony are selected.

Chromosomal DNA transforms competent cells of *Bacillus subtilis* Marburg in higher efficiency than plasmid DNA [T. J. Gryczan et al. J. Bacteriol., 134, 318 (1978); Gryczan and D. Dubnau, Proc. Natl. Acad. Sci. USA 75, 1428 (1978)]. Increased numbers of transformants may be obtained according to the method described by S. Contente and D. Dubnau [Plasmid 2, 555 (1979)], in which the competent cell of *Bacillus subtilis* Marburg are engineered to harbor plasmid containing a partially homologous sequence to a plasmid used for transformation in order to induce homologous recombination. The transformants having γ-glutamyl transpeptidase activity are cultured and the recombinant plasmid DNA is purified by the method described by T. J. Gryczan et al. [J. Bacteriol. 134, 318 (1978)]. Using the probes L and S, Southern blot analysis of the plasmid DNA may indicate whether both sequences, encoding for the two subunits, are present in the plasmid. The source of the cloned sequence of the plasmid may be further examined by nick translation [P. W. J. Rigby et al., J. Mol. Biol., 113, 237 (1977)] and Southern hybridization. Namely, the cloned sequence is radiolabelled and used for hybridization with the chromosomal DNA of SJ138.

Figure 1:
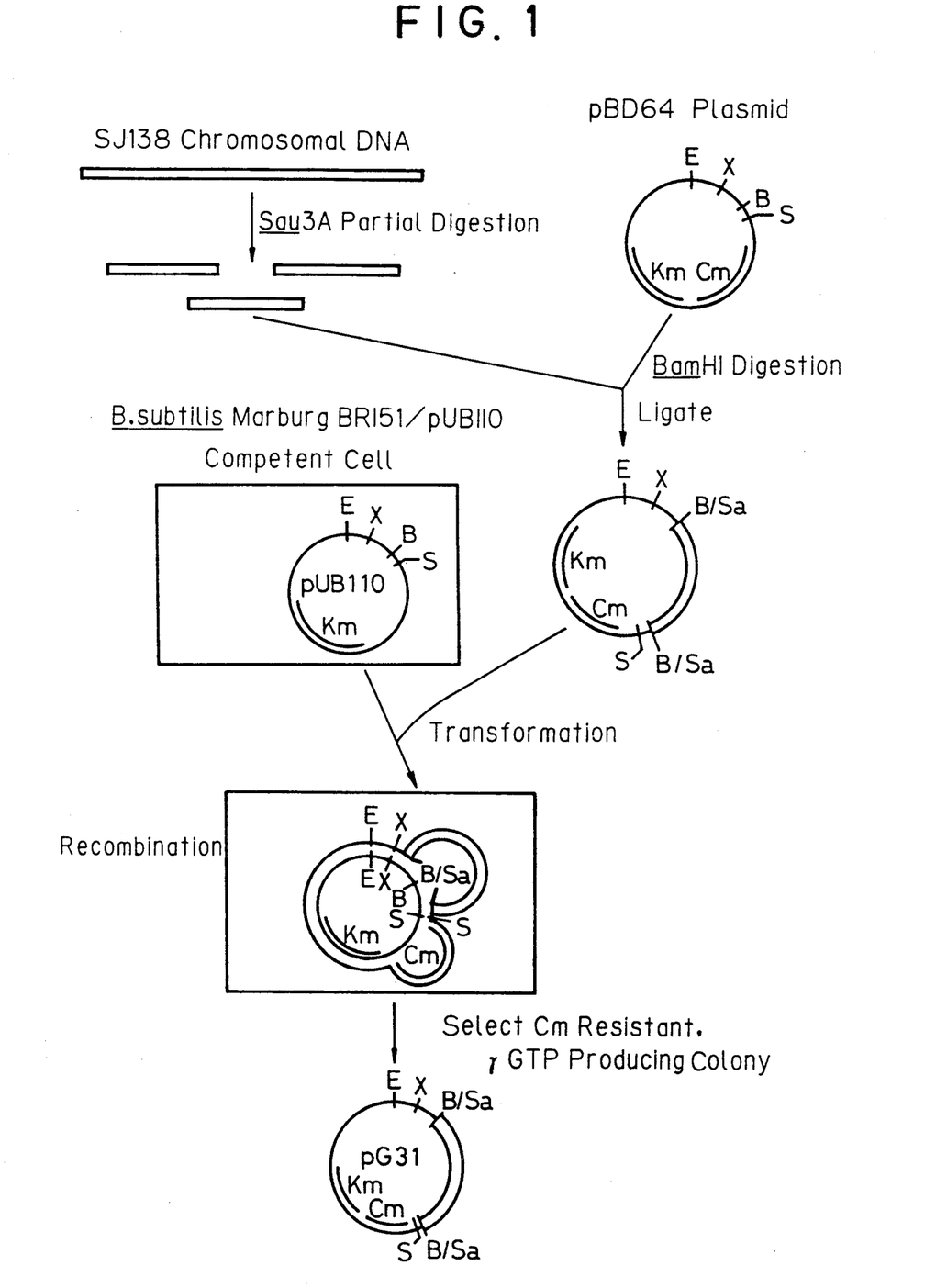
FIG. 1 shows the cloning strategy for cloning a γ-glutamyl transpeptidase gene into a vector of *Bacillus subtilis* and the construction of plasmid pG31.

Next, the BamHI fragment of pBD64 [D. Dubnau et al., J. Bacteriol., 141, 246 (1980)] and the Sau 3A partial digest of SJ138 chromosomal DNA are ligated. The resulting construct may be used to transform *Bacillus subtilis* Marburg harboring pUB110 [T. Gryczan et al., J. Bacteriol., 134, 318 (1978)] which contains a partially homologous sequence to that of pBD64. Recombinant plasmid pG31 containing the γ-glutamyl transpeptidase gene from SJ138 chromosome is thus obtained (See FIG. 1).

The nucleotide sequence of the γ-glutamyl transpeptidase gene in pG31 is confirmed by DNA sequence analysis. The fragment containing the γ-glutamyl transpeptidase gene may be cleaved from pG31, fragmented, and subcloned for the purpose of sequencing. Alternatively, single-stranded DNA may be synthesized from the subclone and sequenced. The sequencing may be carried out using the dideoxy chain termination method [J. Messing, Methods in Enzymology, 101, 20, Academic Press (1983)].

Vieira-Messing plasmids, namely *E. coli* plasmids pUC118 and pUC119 [J. Vieira and J. Messing, Methods in Enzymology, 153, 3 (1987)] may be used as vectors for the subcloning of the γ-glutamyl transpeptidase fragment. The size of the subcloning fragment may be reduced by exonuclease III digestion [S. Henikoff, Gene, 28, 351 (1984)]. The cloning vectors pUC118 and pUC119 contain the intergenic region (IG) of M13 phage [D. Mead and B. Kemper in "Vectors: A Survey of Molecular Cloning Vectors and Their Uses", Butterworth, Mass., (1986)]. Therefore, if the transformant *E. coli* MV1184 is infected with helper phage M13 K07, the IG may mediate the following events: (1) replication of double stranded DNA, (2) synthesis of the ⊕ single-stranded DNA using the ⊖ strand as a template, (3) packaging of the ⊕ single-stranded DNA into the M13 phage coat protein and the budding out of the phage from the bacterial cell. The single-stranded DNA is prepared from the supernatant of the culture of the infected MV1184 and is used in the dideoxy chain termination procedure [J. Vieira and J. Messing, Methods in Enzymology, 153, 3, Academic Press (1987)].

Single-stranded DNA may be also prepared by digesting the γ-glutamyl transpeptidase DNA fragment with restriction enzymes, ligating the resultant DNA fragment with a double-stranded M13mp18 or M13mp19 DNA [C. Yanisch-Perron et al., Gene, 33, 103 (1985)], infecting a suitable *E. coli* host with the recombinant phage, and finally, picking the recombinant plaques and growing them.

The open reading frame (ORF) encoding γ-glutamyl transpeptidase is identified according to the confirmed amino acid sequence and the nucleotide sequence.

The obtained ORF encoding γ-glutamyl transpeptidase DNA is as defined in Sequence Listing by SEQ ID No. 1.

A single ORF has been found in the above DNA fragment according to nucleotide sequence analysis. In the ORF, the signal sequence is upstream (Yamane: Nippon Nogeikagakukai-shi, 61, 64, 1987) to the large subunit and the small subunit. Double digestion of the cloned DNA fragment with SphI and NruI generates a fragment of about 2.4 Kb, which may be used to construct a subclone, free of foreign nucleotide sequences.

The self-clone, free of foreign nucleotide sequences, is constructed as described below.

The vector DNA of the recombinant plasmid pG31 is derived from non-self type plasmid pBD64. The γ-glutamyl transpeptidase DNA fragment may be subcloned into a self-type plasmid from *Bacillus subtilis* origin such as pUB110 and the derivatives thereof. In the examples described below, pEX653, a derivative of pUB110 is used as a self-type plasmid. The vector pEX653 comprises a EcoRI-XbaI fragment of about 4.1 Kb from pUB110 ligated with a chemically synthesized linker copied from the *E. coli* plasmid pUC19. The sequence of the linker is defined in the Sequence Listing by SEQ ID No. 8. Multi-copy plasmid pUG55, which encodes γ-glutamyl transpeptidase and whose host is the *Bacillus subtilis* Marburg BR151 strain, is a recombinant DNA molecule constructed by ligating the SphI-NruI DNA fragment of pG31 which is about 2.4 Kb with the SphI-SmaI fragment of pEX653 (See FIG. 2). The pUG55 may be introduced into SJ138 by the protoplast transformation method [T. Akamatsu and J. Sekiguchi, Agric. Biol. Chem. 46, 1617 (1982)].

*Bacillus subtilis* SJ139 is the strain carrying the recombinant plasmid derived from the genus Bacillus harboring pUG55, which contains the γ-glutamyl transpeptidase gene. The γ-glutamyl transpeptidase gene was derived from *Bacillus subtilis* SJ138 The *Bacillus subtilis* SJ139 strain was deposited with the Fermentation Research Institute, Agency of Industrial Science and Technology under the Budapest Treaty on Dec. 21, 1989 and assigned the accession number FERM BP-2695.

γ-glutamyl transpeptidase can be produced by culturing the *Bacillus subtilis* strain carrying the recombinant plasmid containing a γ-glutamyl transpeptidase gene. The culturing of the microorganism may be carried out according to standard methods known in the art. Namely, the microorganism is cultured in a conventional medium of suitable pH which contains carbon and nitrogen sources, minerals, amino acids, vitamins and the like, aerobically under temperature and pH-control.

The carbon source includes carbohydrates such as glucose, fructose, sucrose, molasses, blackstrap molasses, starch hydrolysate, etc.; alcohols such as ethanol, glycerol, sorbitol, etc.; organic acids such as pyruvic acid, tactic acid, acetic acid, etc.; and amino acids such as glycine, alanine, glutamic acid, aspartic acid, etc. Any material that the microorganism can utilize may be used. The concentration of the carbon source in the culture medium is preferably 5-30% by weight.

The nitrogen source includes various inorganic and organic ammonium salts such as ammonium carbonate, ammonium acetate, ammonium phosphate, etc.; nitrogen containing organic materials such as urea, peptone, NZ amine, meat extract, yeast extract, corn steep liquor, casein hydrolysate, fish meal, digested fish meal, etc, and various amino acids such as glycine, glutamic acid etc. The concentration of the nitrogen source in a culture medium is typically in the range of 0.1 to 10% by weight.

Examples of minerals include potassium dihydrogen phosphate, dipotassium hydrogen phosphate, magnesium sulfate, magnesium phosphate, sodium chloride, ferrous sulfate, manganese sulfate, zinc sulfate, calcium carbonate, and the like. When specific materials such as amino acids, nucleic acids, vitamins, etc., are required for the growth of the microorganism an appropriate amount of these materials may be added to the culture medium.

The culture is grown aerobically by shaking or by aeration and agitation. The temperature for growth preferably ranges from 20°-40° C. The incubation period may be 10-72 hours. It is desirable to keep the pH of the medium around neutral by using ammonia, urea, or sodium hydroxide.

After growth, γ-glutamyl transpeptidase may be recovered from the culture medium using standard methods. The culture is centrifuged, and an organic solvent such as ethanol or acetone and an inorganic salt such as ammonium sulfate is added to the supernatant. The resultant precipitate is then collected.

The present invention will be described in detail in the following Examples which are not to be construed as a restriction of the invention.

EXAMPLE 1

Identification of a Bacillus species that secretes γ-glutamyl transpeptidase 121 strains of the genus Bacillus were plated on BY agar medium [2% powdered bouillon (Kyokuto Seiyaku Kogyo), 0.5% yeast extract (Daigo Eiyo Kagaku), 1.5% agar, and pH 7.2 adjusted with NaOH] and incubated at 30° C. overnight. A platinum loop of the culture was seeded to 5 ml of BYG medium 2% powdered bouillon, 0.5% powdered yeast extract (Daigo Eiyo Kagaku), and 2% glucose, pH 7.2 adjusted with NaOH] and incubated with shaking for 16 hours at 30° C. 0.25 ml of the culture thus obtained was passaged to 5 ml of DGYP medium [2% glycerol, 0.3% powdered yeast extract, 2% peptone, 0.05% potassium dihydrogen phosphate, 0.15% dipotassium hydrogen phosphate, 0.05% magnesium sulfate 7 hydrate 0.002% ferrous sulfate 7 hydrate, 0.002% manganese sulfate 4-6 hydrate, and 100 μg/liter of thiamine hydrochloride, pH 7.2 adjusted with NaOH] and incubated for 48 hours at 30° C.

The resultant culture was centrifuged at 3,000 rpm for 15 minutes and the supernatant was tested for γ-glutamyl transpeptidase activity as described below.

Method of determining γ-glutamyl transpeptidase activity 1 ml of the appropriately diluted supernatant was prewarmed to 30° C. for 2 minutes. To the mixture, 1 ml of the substrate solution [10 mM γ-glutamyl-p-nitroanilide/0.2M Tris-HCl (pH 8.5)], pre-warmed to 30° C., was added to the enzymatic reaction and incubated for 10 minutes at 30° C. The reaction was stopped after 10 minutes by adding 2 ml of 20% acetic acid, followed by centrifugation. The supernatant was analyzed for the amount of p-nitroaniline it contained by using a colorimeter at 410 nm. The control was 2 ml of 20% acetic acid added to 1 ml of the substrate solution and 1 ml of the appropriately diluted supernatent.

1 unit (U) of γ-glutamyl transpeptidase is defined as the amount of the enzyme which generates 1 μM of p-nitroaniline in 1 minute. The following formula is used for the calculation of the enzyme activity:

γ-glutamyl transpeptidase activity (U)=0.523-×(E−Eb)×1/10, where U is γ-glutamyl transpeptidase activity in 1 ml of the diluted supernatant, E is absorbance of samples and Eb is absorbance of the control at 410 nm.

γ-glutamyl transpeptidase activity (U/ml) of the previously discussed Bacillus strains is given in Table 1.

TABLE 1

| Strain | γ-glutamyl transpeptidase activity (U/ml) |
|---|---|
| *Bacillus subtilis* SJ13B | 1.4 |
| *Bacillus subtilis* ATCC 9372 | 0.7 |
| *Bacillus brevis* ATCC 10027 | 0.6 |

EXAMPLE 2

Cloning of the γ-glutamyl transpeptidase gene derived from a *Bacillus subtilis* SJ138 strain (1) Purification of γ-glutamyl transpeptidase produced by *Bacillus subtilis* SJ138

*Bacillus subtilis* SJ138 was streaked on BY agar medium and incubated at 30° C. overnight. One platinum loop of the culture was inoculated into 5 ml of BYG medium and incubated with shaking for 6 hours at 30° C. 0.8 ml of the resultant culture was passaged into 40 mls of BYG medium and incubated with shaking for 10 hours at 30° C. The mixture was introduced into a 2l jar fermenter containing 800 ml of GYP medium [8%, glycerol, 0.3%, yeast extract, 2% peptone, 0.05% potassium hydrogen phosphate, 0.15% dipotassium hydrogen phosphate, 0.05% magnesium sulfate 7 hydrate, 0.002% ferrous sulfate 7 hydrate, 0.0002% manganese sulfate 4-6 hydrate, and 100 µg/liter thiamine hydrochloride, pH 7.2 adjusted with NAOH] and incubated (700 rpm, 1 vvm) for 20 hours at 30° C. The culture was centrifuged at 8,000 rpm for 15 minutes, and an equal volume of ethanol was added to the supernatant. The mixture was placed on ice for an hour and then centrifuged at 8000 rpm for 15 minutes. The precipitate formed was suspended in 80 ml of water. 800 mgs of lysine monohydrochloride was added to the suspension and the mixture was lyophilized at −20° C. in a vacuum. About 1.4 g of the sample thus obtained was resuspended in 50 mM Tris-HCl (TB), pH 7.5 and then dialyzed against TB. After dialysis, the sample was loaded on to a DEAE-cellulose (Serva) column (160 ml capacity) and equilibrated with TB. The column was washed with 500 mls of TB and eluted with 500 mls of TB using a 0-0.5M gradient of NaCl. The fractions eluted were analyzed for γ-glutamyl transpeptidase activity using the procedure described in Example 1. The fractions having γ-glutamyl transpeptidase activity were concentrated using a membrane and the concentrate was dialyzed against 5 mM phosphate buffer, pH 6.8. After dialysis, the sample was loaded on a hydroxyapatite column (60 ml capacity), equilibrated with 5 mm phosphate buffer, pH 6.8, and eluted with 120 mls of 200 mM, 300 mM, and 400 mM phosphate buffer, pH 6.8, respectively. γ-glutamyl transpeptidase activity was found in the 400 mM phosphate eluate. This fraction was dialyzed against TB and then concentrated using a membrane. The concentrate was dialyzed further against TB to give purified γ-glutamyl transpeptidase. The γ-glutamyl transpeptidase thus purified was electrophoresed on a SDS-polyacrylamide gel which yielded two bands of about 41 Kda and 23 Kda, corresponding to the large and small subunits of γ-glutamyl transpeptidase, respectively. No contaminating protein was observed.

(2) Amino acid sequencing of γ-glutamyl transpeptidase

Purified γ-glutamyl transpeptidase was loaded on reverse high pressure liquid chromatography to separate the large and small subunits. Both subunits were trypsinized according to standard methods. The peptide fragments thus produced were fractionated by reverse high pressure liquid chromatography and analyzed using a 470A Sequencer (Applied Biosystems). The amino acid sequence of one of the trypsinized peptides containing both the large and small subunits is shown below. The amino acid sequence from the large subunit is as defined in the Sequence Listing by SEQ ID No. 3. The amino acid sequence from the small subunit is as defined in the Sequence Listing by SEQ ID No. 5.

(3) Synthesis of oligonucleotides corresponding to the amino acid sequence of γ-glutamyl transpeptidase The oligonucleotides shown below were synthesized by a 380A DNA Synthesizer (Applied Biosystems Corp).

Probe L: as defined in the Sequence Listing by SEQ ID No. 4.

Probe S: as defined in the Sequence Listing by SEQ ID No. 6.

(wherein N is A, T, G, or C, Y is T or C, and R is A or G).

To 30 ng of the oligonucleotide thus obtained, a mixture of 30 µCi γ-$^{32}$P-ATP (Amersham), 1 unit of T4 polynucleotide kinase (Takara Shuzo), and 3 µl of kinase buffer (0.5M Tris-HCl, 100 mM MgCl$_2$, and 100 mM dithiothreitol, (pH 7.5) was added. To label the 5' end of the oligomer with $^{32}$P, the resultant mixture (30 µl ) was incubated for 30 minutes at 37° C. 10 µg of salmon DNA was then added and the mixture was extracted with phenol. The extract was loaded on a DEAE Sephadex G-50 (Pharmacia) column equilibrated with 20 mM Tris-HCl (pH 7.5)/100 mM NaCl/1 mM EDTA and eluted to yield the labelled oligomer.

(4) Southern hybridization of the γ-glutamyl transpeptidase gene on chromosomal DNA of SJ138 using probes L and S The γ-glutamyl transpeptidase gene found on chromosomal DNA of SJ138 was detected by Southern hybridization using the probes L and S, as described below.

40 mls of BYG culture medium was inoculated with the SJ138 strain and incubated overnight at 30° C. The chromosomal DNA was prepared from the culture according to the method described by Saito and Miura [H. Saito and K. Miura: Biochim. Biophys. Acta, 72, 619 (1963)]. 2 µg of the chromosomal DNA was digested with EcoRI and HindIII, and the digests were electrophoresed along with a molecular marker λ DNA (Takara Shuzo) on three sets of agarose gel. One of the sets was stained with ethidium bromide and then photographed beside a scale for a comparison of mobility The rest of the gels were immersed consecutively in a 10-fold volume of 0.5N NaOH/1M NaCl, and 0.5M Tris-HCl (pH 7.5)/2.5M NaCl for 30 minutes to allow denaturation. A nitrocellulose filter was placed on each of the gels. The filter/gel was placed in a tray filled with 20×SSC [3M sodium chloride and 0.3M trisodium citrate, (pH 7.0)]. The DNA was left to transfer to the nitrocellulose filter for 16 hours. The filters were then air-dried and baked for two hours at 80° C.

The two filters thus treated were placed in 6 ml of pre-hybridization solution [0.02% Fycoll, 0.02% bovine serum albumin, 0.02% polyvinyl pyrrolidone, 0.9M sodium chloride, 0.09M trisodium citrate, 50 mM Tris-HCl (pH 7.0), and 50 µg/ml of heat denatured salmon sperm DNA] in a vinyl bag, and prehybridized for 3 hours at 65° C. After pre-hybridization, the filters were removed from the bag and each was placed in a separate bag. 3 mls of fresh pre-hybridization solution was then added to each bag, and 2 µCi of each of the $^{32}$P-labelled probes L and S, previously heated for 5 minutes at 95° C., was added separately to each of the bags. The bags were incubated for 16 hours at 34° C. After hybridization, the filters were removed from each bag and washed 3× with a 100 mls of 6×SSC [0.9M sodium chloride and 0.09M trisodium citrate (pH 7.0)] for 10 minutes at 20° C. The filters were airdried and exposed to X-ray film for two days at −80° C. The film was developed and the bands that appeared on the film were compared with those on the photograph of the gel. The analysis illustrated that the probes L and S hybridized to the 2.9 Kb EcoRI fragment and the 2.8 Kb HindIII fragment.

(5) Cloning of the γ-glutamyl transpeptidase gene using a *Bacillus subtilis* host-vector system Since the nucleotide sequence encoding the two subunits of γ-glutamyl transpeptidase can be cloned as a single insert, as shown from the results described above, "shot gun cloning" was carried out using a *Bacillus subtilis* host-vector system. The *Bacillus subtilis* Marburg BR151 strain was first transformed with pUB110 derived from *Bacillus subtilis*. The transformant was designated BR151/pUB110 and used as a host. The plasmid pBD64, [D. Dubnau et al., J. Bacteriol., 141, 246 (1980)] derived from *Bacillus subtilis* was digested with BamHI and ligated with the chromosomal DNA of the SJ138 strain partially digested with Sau3A, using T4 DNA ligase (Takai, Shuzo). The construct was used to transform the BR151/pUB110 strain. The transformant was plated on a nitrocellulose filter on GT agar medium [0.2% maltose, 0.25% monosodium glutamate, 50 μg/ml of tryptophan, 0.05% potassium dihydrogen phosphate, 0.15% dipotassium hydrogen phosphate, 0.05% magnesium sulfate 7 hydrate, 0.002% ferrous sulfate 7 hydrate, 0.002% manganese sulfate 4–6 hydrate 100 μ g/liter of thiamine hydrochloride, and 1.5% agar, (pH 7.2 adjusted with NaOH)] containing 5 μg/ml of chloramphenicol (Cm), and incubated for three days at 30° C. After a colony appeared on the filter, the filter was placed on a filter pre-soaked with 5 mM γ-glutamyl-p-nitroanilide/ 0.2M Tris-HCl (pH 8.5), and incubated at 37° C. Certain colonies showed a yellow pigment around them, suggesting that p-nitroaniline was formed by catalytic action of γ-glutamyl transpeptidase from the substrate γ-glutamyl-p-nitroanilide.

A plasmid designated pG31 was obtained from one of those colonies according to the method described by Gryczan et al. [T. J. Gryczan et al., J. Bacteriol., 134, 318 (1978)]. Southern hybridization of pG31 was carried out using the $^{32}$P-labelled probes L and S according to the method described in Examples (2), (3), and (4). The results demonstrated that certain a DNA sequence on pG31 hybridized to both probes, suggesting that pG31 contained the cloned nucleotide sequences of the large and small subunits of γ-glutamyl transpeptidase gene.

Southern hybridization of the chromosomal DNA of SJ138 was carried out using a 1.0 Kb EcoRI fragment of pG31 as a probe to determine the source of the cloned insert in pG31. 5 μg of pG31 DNA was digested with EcoRI and electrophoresed on an agarose gel. The 1.0 Kb EcoRI band was excised from the gel and placed in a dialysis tube. 0.3 ml of Tris-borate (90 mM Tris-borate and 4 mM EDTA, pH 8.3) was added to the tube, and the tube was sealed and placed in a vessel filled with the same Tris-borate. Electroelution was carried out at 50 mA for 10 min. The current was then reversed for 20 seconds to detach any DNA adhering to the dialysis tube. The DNA suspension was removed from the tube. A 1/10 volume of 3M sodium acetate, pH 5.6 and 3× volume of ice cold ethanol were then added to the DNA suspension. The mixture was centrifuged and the pelleted DNA was recovered. The DNA was dried and resuspended in 10 μl of TE buffer (20 mM Tris-HCl, 1 mM EDTA, pH 7.5).

The DNA thus obtained was radiolabelled by nick translation [P. W. J. Rigby et al., J. Mol. Biol., 113, 237 (1977)]. Southern hybridization of a BglII digest of the SJ138 chromosomal DNA and *Bacillus subtilis* Marburg BR115 DNA, was carried out using the above labelled fragment as a probe. The 9.5 Kb BglII digest of the SJ138 chromosomal DNA showed a high degree of hybridization, while that of BR151 showed poor hybridization. The results demonstrated that the DNA insert in pG31 was derived from the chromosomal DNA of the SJ138 strain.

Figure 3:
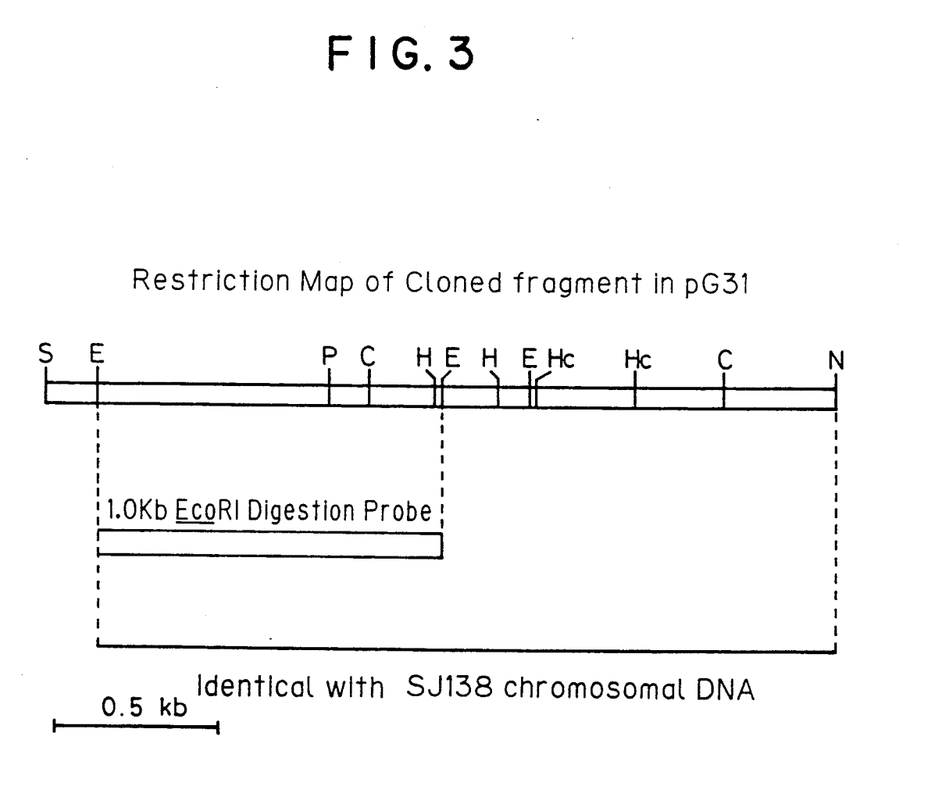
FIG. 3 is a restriction map of the cloned γ-glutamyl transpeptidase gene in pG31.

Furthermore, Southern hybridization of pG31 DNA and SJ138 chromosomal DNA which were digested with various restriction enzymes was carried out using the above labelled 1.0 Kb EcoRI fragment as a probe. The 2.1 Kb of the EcoRI-NruI region on the chromosomal DNA of SJ138 was found to be identical with that of the cloned DNA fragment in pG31 (See FIG. 3).

EXAMPLE 3

Determination of the DNA sequence of the γ-glutamyl transpeptidase gene

To determine the nucleotide sequence of the γ-glutamyl transpeptidase gene, pG31 was digested with various restriction enzymes which were then cloned into pUC118 and pUC119. The sizes of the fragments were reduced using an exonuclease III deletion kit (Takara Shuzo) when necessary.

The constructs thus obtained were used for the transformation of MV1184, an *E. coli* K12 substrain. The transformant was cultured in 2X TY medium (1.6% bactotrypton, 1% yeast extract, and 0.5% NaCl, pH 7.4) containing 100 μg/ml of Ampicillin overnight at 37° C. 30 μl of the overnight culture was added to 3 ml of 2X TY medium containing 100 μg/ml of Ampicillin, and incubated for three hours at 37° C. Helper phage M13KO7 was then added to the mixture at M.O.I.=3. Simultaneously, Kanamycin (Km) was added to a final concentration of 70 μg/ml, and the mixture was further incubated overnight at 37° C. Single-stranded DNA was prepared from the phage particles [J. Vieira and J. Messing: Methods in Enzymology, 153, 3, Academic Press (1987)] and used for DNA sequencing by the dideoxy chain termination method. 2382 bases of the nucleotide sequence from the SphI to the NruI restriction site, were determined as above, and are defined in the Sequence Listing by SEQ ID No. 2.

−35 and −10 is the presumed promoter region. RBS is the presumed ribosome binding site. →←  is the presumed transcription terminal sequence.

Open reading frame 1 (ORF1), encoding 591 amino acids has been found within the nucleotide sequence between the SphI and NruI recognition sites. A complementary sequence AAAGGAGG to that of the 3' end of *Bacillus subtilis* 16S ribosomal RNA has been found upstream in the ORF1 and the sequence is believe to be a ribosome binding site. Upstream to the ribosome binding site is the presumed −35 sequence (AAAACA) and −10 sequence (TATAAT). Furthermore, a potential stem loop structure as defined in the Sequence Listing of SEQ ID No. 9, which is believed to be involved in transcriptional termination, has been found downstream in the ORF1. However, the nucleotide sequence controlling gene expression has not been found within the ORF1.

Amino acids 1–30 of the ORF1 have a typical signal sequence found in the genus Bacillus (Yamane, Nippon Nogeikagakukai-shi, 61, 64, 1987), and is the only signal sequence found in the ORF1. The sequence of amino acids 378 to 390 is identical with the partial amino acid sequence of the large subunit, and the amino acid sequence of 503 to 510 is identical with the partial sequence of the small subunit. Taken together, these findings indicate that the γ-glutamyl transpeptidese gene of the *Bacillus subtilis* SJ138 strain encodes both the large and small subunits of γ-glutamyl transpeptidese as a single polypeptide.

234 nucleotide bases out of 235 bases, starting from the SphI recognition site of the nucleotide sequence of pG31 are identical with the nucleotide numbered 789-1023 of pUB110 [T. McKenzie et al., Plasmid, 15, 93 (1986)] with the one exception being G at nucleotide number 860. The nucleotides numbered 230-234 on pG31, a BamHI and Sau3 A recognition site, is also believed to be one of the ligation sites. An EcoRI site is located 40 nucleotides downstream of the said ligation site of pG31. A NruI site is located 2142 nucleotides downstream of the ligation site. The site 14 nucleotides away from the NruI site on pG31 is believed to be the other ligation site, a Sau3A/BamHI site, and the sequence following the site is the same sequence found upstream of nucleotide number 788 in pUB110.

The results described above and in Example 2 (5) demonstrate that the 2382 base long sequence, between the SphI and Nru1 recognition site of pG31, is solely derived from the nucleotide sequence of pUB110 and SJ138 chromosomal DNA. The self-cloning of the γ-glutamyl transpeptidase gene is achieved by cloning the 2383 base long sequence into a plasmid vector derived from Bacillus subtilis.

EXAMPLE 4

Figure 2:
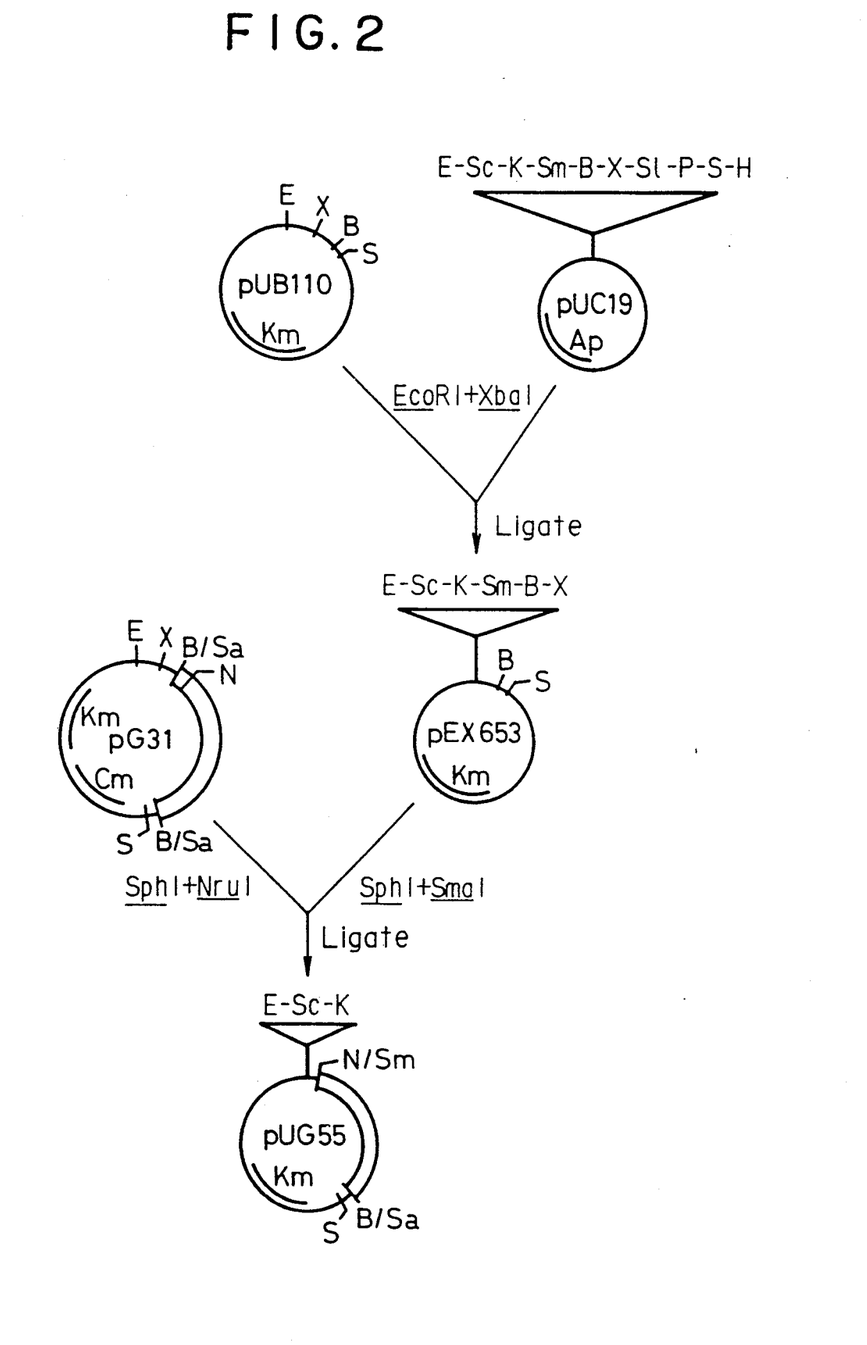
FIG. 2 shows a method of constructing plasmids pEX653 and pUG55.

Construction of a transformant containing multiple copies of the γ-glutamyl transpeptidase gene To carry out self-cloning, the SphI-NruI fragment of pG31 containing the gene was inserted into the vector pEX653, a derivative of Bacillus subtilis pUB110. The vector pEX653 was constructed as shown in FIG. 2 and described below. 5 μg of Bacillus subtilis plasmid pUB110 DNA and 5 μg of E. coli plasmid pUC19 and ligated using T4 DNA Ligase. The resultant construct was used to transform Bacillus subtilis Marburg BR151. The transformant was screened on BY agar medium containing 5 μg/ml of Kanamycin (Km). A transformant with the plasmid DNA with Km resistance was prepared according to the method described in Example 2 (5). The plasmid pEX653 thus obtained was confirmed as containing the partial multi-linker site, EcoRI-SacI-KonI -SmaI-BamHI-XbaI, derived from pUC19 in place of the EcoRI-XbaI fragment of pUB110.

Subcloning of the γ-glutamyl transpeptidase gene into pEX653 was carried out as follows. 5 μg of pEX653 DNA was digested with SphI and SmaI, extracted with phenol, and precipitated with ethanol to recover the DNA fragments. In the meantime, 5 μg of pG31 DNA was digested with SphI and NruI, extracted with phenol and precipitated with ethanol. The pEX653 and pG31 restriction fragments were suspended seperately in TE buffer, mixed and ligated using T4 DNA ligase. The construct was used to transform Bacillus subtilis Marburg BR151. The transformants were screened on a nitrocellulose filter on GT agar medium containing 5 μg/ml of Km according to the method described in Example 2 (5). A colony showing γ-glutamyl transpeptidase activity was picked and cultured. Plasmid DNA was prepared according to the method described in 2 (5), digested with a restriction enzyme and electrophoresed on an agarose gel for analysis.

One of the plasmids, designated pUG55, contains a SphI-NruI fragment of about 2.4 Kb encoding γ-glutamyl transpeptidase at the SphI-SmaI site of pEX653 (See FIG. 2).

pUG55 was introduced into protoplast of Bacillus subtilis SJ138, a strain producing γ-glutamyl transpeptidase according to the method described by Akamatsu and Sekiguchi [T. Akamatsu and J. Sekiguchi: Agric. Biol. Chem., 46. 1617 (1982)]. The transformant was screened on a minimum essential medium containing 100 μg/ml of Km. The colony grown on the plate was picked and cultured. Plasmid DNA was prepared as described in Example 2 (5), digested with a restriction enzyme, electrophoresed on agarose gel and analyzed. The plasmid DNA as prepared above was found to be identical with the plasmid DNA used for transformation.

EXAMPLE 5

Production of γ-glutamyl transpeptidase using various transformants

The production of γ-glutamyl transpeptidase in various strains was tested: Bacillus subtilis Marburg BR151 alone, BR151 containing pG31, BR151 containing pEX653, BR151 containing pUG55, Bacillus subtilis SJ138 alone, SJ138 containing pEX653, SJ138 containing pUG55. Each strain was plated on BY agar medium and incubated at 30° C. overnight. One platinum loop of the culture was seeded to 3 ml of BYG medium and incubated at 30° C. overnight. 0.25 ml of the resultant culture was added to 5 ml of GYP medium in a tube. The mixture was incubated for 72 hours at 30° C. In the case of the strains containing a plasmid, Kanamycin was added to both the BYG and GYP media to a final concentration of 5 μg/ml. After incubation, the culture was centrifuged to remove the bacterial cells and the supernatant was tested for γ-glutamyl transpeptidase activity calorimetrically as described in Example 1. The glutamyl transpeptidase production of various strains is given in Table 2.

TABLE 2

| Strain | γ-Glutamyl Transpeptidase Activity (U/ml) |
|---|---|
| Bacillus subtilis Marburg | |
| BR151 | 0 |
| BR151/pG31 | 45.6 |
| BR151/pEX653 | 0 |
| BR151/pUG55 | 48.5 |
| Bacillus subtilis | |
| SJ138 (FERM BP-2694) | 3.0 |
| SJ138/pEX653 | 2.8 |
| SJ138/pUG55 (SJ139, FERM BP-2695) | 73.5 |

The culture was incubated in BYG(3 ml) medium at 30° C. overnight. Then 0.25 ml of the culture in BYG was incubated in GYP (5 ml) medium at 30° C. for 72 hr.

Introduction of a recombinant plasmid containing a γ-glutamyl transpeptidase gene into a γ-glutamyl transpeptidase non-producing or producing strain causes production or an increase in γ-glutamyl transpeptidase production, respectively, as shown in Table 2.

Various references are cited herein, the disclosures of which are incorporated by reference in their entireties.

---

What is claimed is:

1. A process for producing enhanced levels of γ-glutamyl transpeptidase, which comprises culturing in a culture medium a microorganism belonging to the genus Bacillus and carrying a recombinant DNA comprised of cloning vector DNA and a DNA fragment which contains a gene coding for γ-glutamyl transpeptidase, said gene obtained from *Bacillus subtilis* and operably linked to a transcriptional promoter, accumulating γ-glutamyl transpeptidase in the culture and recovering γ-glutamyl transpeptidase therefrom.

2. A process according to claim 1 wherein the gene coding for γ-glutamyl transpeptidase has the nucleotide sequence as defined in the Sequence Listing by SEQ ID: No. 1.

3. An isolated gene which codes for γ-glutamyl transpeptidase and has the nucleotide sequence as defined in the Sequence Listing by SEQ ID: No. 1.

4. A recombinant DNA comprised of cloning vector DNA and a DNA fragment containing a gene coding for γ-glutamyl transpeptidase, said gene obtained from *Bacillus subtilis*.

5. A microorganism belonging to the genus Bacillus and carrying a recombinant DNA comprised of cloning vector DNA and a DNA fragment which contains a gene coding for γ-glutamyl transpeptidase, said gene obtained from *Bacillus subtilis*.

6. A microorganism according to claim 5 which is a *Bacillus subtilis* SJ139 (FERM BP-2695).

7. A process for producing γ-glutamyl transpeptidase, which comprises culturing in a culture medium a microorganism belonging to the genus Bacillus and carrying a recombinant DNA comprised of cloning vector DNA and a DNA fragment which contains a gene coding for γ-glutamyl transpeptidase, said gene obtained from *Bacillus subtilis* and operably linked to a transcriptional promoter, accumulating in the culture γ-glutamyl transpeptidase in an amount which is at least as high as ten times that of the microorganism not containing said recombinant DNA, and recovering γ-glutamyl transpeptidase therefrom.

* * * * *

SEQUENCE LISTING (1) GENERAL INFORMATION:
  (i) APPLICANT: KATSUMATA, RYOICHI MIZUKAMI, TORU
OHTA, SHIGENORI
SATO, MORIYUKI
YAMAGUCHI, KAZUO
(ii) TITLE OF INVENTION: PROCESS FOR THE PRODUCTION OF GAMMA-GLUTAMYL TRANSPEPTIDASE
(iii) NUMBER OF SEQUENCES: 9
(iv) CORRESPONDENCE ADDRESS:
   (A)   ADDRESSEE: PENNIE & EDMONDS
   (B)   STRRET: 1155 AVENUE OF THE AMERICAS
   (C)   CITY: NEW YORK
   (D)   STATE: N.Y.
   (E)   COUNTRY: U.S.A.
   (F)   ZIP: 10036
(v) COMPUTER READABLE FORM:
   (A)   MEDIUM TYPE: Floppy disk
   (B)   COMPUTER: IBM PC compatible
   (C)   OPERATING SYSTEM: PC-DOS/MS-DOS
   (D)   SOFTWARE: PatentIn Release #1.0, Version #1.25
(vi) CURRENT APPLICATION DATA:
   (A)   APPLICATION NUMBER: US 07/652,151
   (B)   FILING DATE: 07-FEB-1991
   (C)   CLASSIFICATION:
(viii) ATTORNEY/AGENT INFORMATION:
   (A)   NAME: MISROCK, S. LESLIE
   (B)   REGISTRATION NUMBER: 18,872
   (C)   REFERENCE/DOCKET NUMBER: 7005-021-999
(ix) TELECOMMUNICATION INFORMATION:
   (A)   TELEPHONE: 212-790-9090
   (B)   TELEFAX: 212-879-9741
(2) INFORMATION FOR SEQ ID NO:1:
   (i) SEQUENCE CHARACTERISTICS:
      (A)   LENGTH: 1773 base pairs
      (B)   TYPE: nucleic acid
      (C)   STRANDEDNESS: single
      (D)   TOPOLOGY: linear
   (ii) MOLECULE TYPE: DNA (genomic)
   (vi) ORIGINAL SOURCE:
      (A)   ORGANISM: *Bacillus subtillis*
      (B)   STRAIN: SJ138 (FERM BP-2694)
   (xi) SEQUENCE DESCRIPTION: SEQ ID NO:1:

```
ATGAAAAAGA  AAAAGTTTAT  GAATCTCTGT  TTTATCGTTC  TGCTCAGTAC  TTTGCTCGCG    60
GCCGGAAGCA  TCCCTTATCA  CGCTCAGGCT  AAGAAACACC  CGTTTTCCTA  TGACGACTAC   120
AAACAGGTAG  ATGTCGGCAA  AGACGGCATG  GTTGCCACCG  CCCATCCTCT  CGCTTCACAA   180
ATCGGTGCCG  ACGTGCTGAA  AAAAGGCGGC  AATGCAATGG  ACGCCGCGGT  TGCCATTCAA   240
TTCGCATTAA  ACGTAACTGA  ACCTTAGATG  TCTGGAATCG  GCGGCGGCGG  ATTTATGATG   300
GTTTATGATG  CGAAGACGAA  AGACACCACC  ATTATCGACA  GCAGGGAACG  CGCACCGGCA   360
GGCGCAACAC  CGGATATGTT  CCTTGACGAA  AACGGCAAAG  CCATTCCTTT  CTCCGAACGC   420
GTTACGAAAG  GGACTGCAGT  CGGTGTTCCG  GGAACATTAA  AAGGACTTGA  AAAAGCGCTA   480
GACAAATGGG  GCACACGCTC  CATGAAACAA  CTCATCACCC  CTTCCATTAA  ACTTGCCTCA   540
AAAGGCTTTC  CGATCGATTC  GGTTTTAGCT  GATGCCATCT  CAGATTATAA  AGACAAATTA   600
TCACACACTG  CTGCAAAAGA  CGTGTTTCTT  CCGGACGGAG  AACCTCTGAA  AGAAGGAGAC   660
ACACTCATCC  AAAAAGACTT  AGCCAAAACA  TTTACAGCTA  TTAAGTACAA  AGGCACAAAA   720
GCATTCTATG  ACGGTGCATT  CTCCAAAAAG  CTTGCAGAAA  CAGTGCAGGA  ATTCGGCGGC   780
TCAATGACAG  AAAAAGACAT  TAAAAACTTC  AATGTGACGA  TTGACGAACC  GATCTGGGGA   840
GATTACCAGG  GCTATCATAT  CGCAACTGCT  CCTCCTCCAA  GCTCGGGCGG  TGTTTTCCTG   900
TTGCAAATGC  TGAACCTCCT  GGATGATTTT  AAGCTTTCTC  AATATGATAT  CCGTTCTTGG   960
CAAAAATATC  AGCTTCTCGC  AGAAACGATG  CATTTGGCTT  ATGCTGACCG  CGCCGCATTT  1020
GCCGGGGACC  CAGAATTCGT  CAACGTCCCT  CTCAAAGGTC  TCTTGAATCC  AGATTATATC  1080
AATGCCCGCA  GACAGCTGAT  AGATATTGAT  AAAGTCAATA  AAAAACCGAA  AGCCGGCGAT  1140
CCTTGGGCCT  ATCAGGAAGG  TTCTGCAAAC  TATAAACAAG  TGGAGCAGCC  GACTGACAAA  1200
```

-continued

| | | | | | | |
|---|---|---|---|---|---|---|
| CAAGAAGGTC | AAACGACTCA | CTTCACGGTA | ACCGACCGCT | TCGGCAATGT | CGTATCTTAT | 1260 |
| ACGACAACAA | TTGAACAGCT | GTTCGGTTCC | GGCATTATGG | TTCCCGGATA | CGGCGTTGTG | 1320 |
| CTGAATAATG | AGTTAACAGA | CTTCGATGCG | GTGCCTGGCG | GCGCAAATGA | AGTGCAGCCG | 1380 |
| AATAAACGTC | CGCTCAGCAG | CATGACTCCG | ACTATTTTAT | TCAAAAATAA | CGAACCTGTC | 1440 |
| CTGACTGTCG | GCTCCCCCGG | CGGAGCAACG | ATTATTTCTT | CCGTCCTGCA | AACGATCCTG | 1500 |
| AACAAAGTTG | AGTACGGCAT | GGATCTGAAA | GCGGCAGTCG | AAGAGCCGAG | AATTTACACA | 1560 |
| AACAGCATGA | CATCCTATCG | ATATGAAAAA | GGAGTGCCGG | AAGAAGCCCG | CACAAAACTG | 1620 |
| AACGAAATGG | GGCATAAATT | CGGCAGCAGC | CCGGTTGATA | TCGGTAATGT | GCAAAGCATC | 1680 |
| CTGATCGACC | GTGAAAACGG | CACCTTCACC | GGAGTCGCCG | ACTCAAGCCG | AAACGGAGCC | 1740 |
| GCAATCGGCG | TAAACTTGAA | AAATTATAAA | AAA | | | 1773 |

(2) INFORMATION FOR SEQ ID NO:2:
    (i) SEQUENCE CHARACTERISTICS:
        (A)    LENGTH: 2382 base pairs
        (B)    TYPE: nucleic acid
        (C)    STRANDEDNESS: single
        (D)    TOPOLOGY: linear
    (ii) MOLECULE TYPE: DNA (genomic)
    (vi) ORIGINAL SOURCE:
        (A)    ORGANISM: *Bacillus subtilis*
        (B)    STRAIN: SJ138 (FERM BP-2694)
    (ix) FEATURE:
        (A)    NAME/KEY: −35_signal
        (B)    LOCATION: 430 . . . 435
    (ix) FEATURE:
        (A)    NAME/KEY: −10_signal
        (B)    LOCATION: 453 . . . 458
    (ix) FEATURE:
        (A)    NAME/KEY: RBS
        (B)    LOCATION: 473 . . . 480
    (ix) FEATURE:
        (A)    NAME/KEY: CDS
        (B)    LOCATION: 487 . . . 2259
    (xi) SEQUENCE DESCRIPTION: SEQ ID NO:2:

| | | | | | | |
|---|---|---|---|---|---|---|
| GCATGCAATT | TCATAATCAA | AGAGAGCGAA | AAAGTAGAAC | GAATGATGAT | ATTGACCATG | 60 |
| AGCGAACACG | TGAAAATTAT | GATTTGAAAA | ATGATAAAAA | TATTGATTAC | AACGAACGTG | 120 |
| TCAAAGAAAT | TATTGAATCA | CAAAAAACAG | GTACAAGAAA | AACGAGGAAA | GATGCTGTTC | 180 |
| TTGTAAATGA | GTTGCTAGTA | ACATCTGACC | GAGATTTTTT | TGAGCAACTG | GATCGTTAAA | 240 |
| TACTGGCTCA | CGTTCCTTCA | TATGTCATGT | GAGTGAATTC | TGTTTTGTTT | ATTGTAGCTT | 300 |
| ATTTTTTGTC | TTTATGCTTG | TTTCACAGCT | TTTTCAGTCC | GGTTTCCCAT | TTAGCCTATT | 360 |
| TGCGACTGAT | TACATTCACA | CAGAAACCCC | AACTTTTTGC | ACACCGGACT | ATTCCGTTTG | 420 |
| TCACTTGTGA | AAACAGCACA | TTTTACTTAC | TCTATAATTG | TAAGCGGAAA | ACAAAGGAGG | 480 |

```
CAGACT ATG AAA AAG AAA AAG TTT ATG AAT CTC TGT TTT ATC GTT CTG               528
       Met Lys Lys Lys Lys Phe Met Asn Leu Cys Phe Ile Val Leu
        1           5                  10

CTC AGT ACT TTG CTC GCG GCC GGA AGC ATC CCT TAT CAC GCT CAG GCT              576
Leu Ser Thr Leu Leu Ala Ala Gly Ser Ile Pro Tyr His Ala Gln Ala
 15              20                  25                  30

AAG AAA CAC CCG TTT TCC TAT GAC GAC TAC AAA CAG GTA GAT GTC GGC              624
Lys Lys His Pro Phe Ser Tyr Asp Asp Tyr Lys Gln Val Asp Val Gly
                 35                  40                  45

AAA GAC GGC ATG GTT GCC ACC GCC CAT CCT CTC GCT TCA CAA ATC GGT              672
Lys Asp Gly Met Val Ala Thr Ala His Pro Leu Ala Ser Gln Ile Gly
             50                  55                  60

GCC GAC GTG CTG AAA AAA GGC GGC AAT GCA ATT GAC GCC GCG GTT GCC              720
Ala Asp Val Leu Lys Lys Gly Gly Asn Ala Ile Asp Ala Ala Val Ala
         65                  70                  75
```

-continued

| | | | | | | | | | | | | | | | | |
|---|---|---|---|---|---|---|---|---|---|---|---|---|---|---|---|---|
| ATT | CAA | TTC | GCA | TTA | AAC | GTA | ACT | GAA | CCT | ATG | ATG | TCT | GGA | ATC | GGC | 768 |
| Ile | Gln 80 | Phe | Ala | Leu | Asn | Val 85 | Thr | Glu | Pro | Met | Met 90 | Ser | Gly | Ile | Gly | |
| GGC | GGC | GGA | TTT | ATG | ATG | GTT | TAT | GAT | GCG | AAG | ACG | AAA | GAC | ACC | ACC | 816 |
| Gly 95 | Gly | Gly | Phe | Met | Met 100 | Val | Tyr | Asp | Ala | Lys 105 | Thr | Lys | Asp | Thr | Thr 110 | |
| ATT | ATC | GAC | AGC | AGG | GAA | CGC | GCA | CCG | GCA | GGC | GCA | ACA | CCG | CAT | ATG | 864 |
| Ile | Ile | Asp | Ser | Arg 115 | Glu | Arg | Ala | Pro | Ala 120 | Gly | Ala | Thr | Pro | Asp 125 | Met | |
| TTC | CTT | GAC | GAA | AAC | GGC | AAA | GCC | ATT | CCT | TTC | TCC | GAA | CGC | GTT | ACG | 912 |
| Phe | Leu | Asp | Glu 130 | Asn | Gly | Lys | Ala | Ile 135 | Pro | Phe | Ser | Glu | Arg 140 | Val | Thr | |
| AAA | GGG | ACT | GCA | GTC | GGT | GTT | CCG | GGA | ACA | TTA | AAA | GGA | CTT | GAA | AAA | 960 |
| Lys | Gly | Thr 145 | Ala | Val | Gly | Val | Pro | Gly 150 | Thr | Leu | Lys | Gly 155 | Leu | Glu | Lys | |
| GCG | CTA | GAC | AAA | TGG | GGC | ACA | CGC | TCC | ATG | AAA | CAA | CTC | ATC | ACC | CCT | 1008 |
| Ala | Leu 160 | Asp | Lys | Trp | Gly | Thr 165 | Arg | Ser | Met | Lys | Gln 170 | Leu | Ile | Thr | Pro | |
| TCC | ATT | AAA | CTT | GCC | TCA | AAA | GGC | TTT | CCG | ATC | GAT | TCG | GTT | TTA | GCT | 1056 |
| Ser 175 | Ile | Lys | Leu | Ala | Ser 180 | Lys | Gly | Phe | Pro | Ile 185 | Asp | Ser | Val | Leu | Ala 190 | |
| GAT | GCC | ATC | TCA | GAT | TAT | AAA | GAC | AAA | TTA | TCA | CAC | ACT | GCT | GCA | AAA | 1104 |
| Asp | Ala | Ile | Ser | Asp 195 | Tyr | Lys | Asp | Lys | Leu 200 | Ser | His | Thr | Ala | Ala 205 | Lys | |
| GAC | GTG | TTT | CTT | CCG | GAC | GGA | GAA | CCT | CTG | AAA | GAA | GGA | GAC | ACA | CTC | 1152 |
| Asp | Val | Phe | Leu 210 | Pro | Asp | Gly | Glu | Pro 215 | Leu | Lys | Glu | Gly | Asp 220 | Thr | Leu | |
| ATC | CAA | AAA | GAC | TTA | GCC | AAA | ACA | TTT | ACA | GCT | ATT | AAG | TAC | AAA | GGC | 1200 |
| Ile | Gln | Lys 225 | Asp | Leu | Ala | Lys | Thr 230 | Phe | Thr | Ala | Ile | Lys 235 | Tyr | Lys | Gly | |
| ACA | AAA | GCA | TTC | TAT | GAC | GGT | GCA | TTC | TCC | AAA | AAG | CTT | GCA | GAA | ACA | 1248 |
| Thr | Lys 240 | Ala | Phe | Tyr | Asp | Gly 245 | Ala | Phe | Ser | Lys | Lys 250 | Leu | Ala | Glu | Thr | |
| GTG | CAG | GAA | TTC | GGC | GGC | TCA | ATG | ACA | GAA | AAA | GAC | ATT | AAA | AAC | TTC | 1296 |
| Val 255 | Gln | Glu | Phe | Gly | Gly 260 | Ser | Met | Thr | Glu | Lys 265 | Asp | Ile | Lys | Asn | Phe 270 | |
| AAT | GTG | ACG | ATT | GAC | GAA | CCG | ATC | TGG | GGA | GAT | TAC | CAG | GGC | TAT | CAT | 1344 |
| Asn | Val | Thr | Ile | Asp 275 | Glu | Pro | Ile | Trp | Gly 280 | Asp | Tyr | Gln | Gly | Tyr 285 | His | |
| ATC | GCA | ACT | GCT | CCT | CCT | CCA | AGC | TCG | GGC | GGT | GTT | TTC | CTG | TTG | CAA | 1392 |
| Ile | Ala | Thr | Ala 290 | Pro | Pro | Pro | Ser | Ser 295 | Gly | Gly | Val | Phe | Leu 300 | Leu | Gln | |
| ATG | CTG | AAC | CTC | CTG | GAT | GAT | TTT | AAG | CTT | TCT | CAA | TAT | GAT | ATC | CGT | 1440 |
| Met | Leu | Asn 305 | Leu | Leu | Asp | Asp | Phe 310 | Lys | Leu | Ser | Gln | Tyr 315 | Asp | Ile | Arg | |
| TCT | TGG | CAA | AAA | TAT | CAG | CTT | CTC | GCA | GAA | ACG | ATG | CAT | TTG | GCT | TAT | 1488 |
| Ser | Trp 320 | Gln | Lys | Tyr | Gln | Leu 325 | Leu | Ala | Glu | Thr | Met 330 | His | Leu | Ala | Tyr | |
| GCT | GAC | CGC | GCC | GCA | TTT | GCC | GGG | GAC | CCA | GAA | TTC | GTC | AAC | GTC | CCT | 1536 |
| Ala 335 | Asp | Arg | Ala | Ala | Phe 340 | Ala | Gly | Asp | Pro | Glu 345 | Phe | Val | Asn | Val | Pro 350 | |
| CTC | AAA | GGT | CTC | TTG | AAT | CCA | GAT | TAT | ATC | AAT | GCC | CGC | AGA | CAG | CTG | 1584 |
| Leu | Lys | Gly | Leu | Leu 355 | Asn | Pro | Asp | Tyr | Ile 360 | Asn | Ala | Arg | Arg | Gln 365 | Leu | |
| ATA | GAT | ATT | GAT | AAA | GTC | AAT | AAA | AAA | CCG | AAA | GCC | GGC | GAT | CCT | TGG | 1632 |
| Ile | Asp | Ile | Asp 370 | Lys | Val | Asn | Lys | Lys 375 | Pro | Lys | Ala | Gly 380 | Asp | Pro | Trp | |

| | | | | | | | | | | | | | | | |
|---|---|---|---|---|---|---|---|---|---|---|---|---|---|---|---|
| GCC | TAT | CAG | GAA | GGT | TCT | GCA | AAC | TAT | AAA | CAA | GTG | GAG | CAG | CCG | ACT |
| Ala | Tyr | Gln | Glu | Gly | Ser | Ala | Asn | Tyr | Lys | Gln | Val | Glu | Gln | Pro | Thr |
|  |  | 385 |  |  |  |  | 390 |  |  |  |  | 395 |  |  |  |

1680

| GAC | AAA | CAA | GAA | GGT | CAA | ACG | ACT | CAC | TTC | ACG | GTA | ACC | GAC | CGC | TTC |
|---|---|---|---|---|---|---|---|---|---|---|---|---|---|---|---|
| Asp | Lys | Gln | Glu | Gly | Gln | Thr | Thr | His | Phe | Thr | Val | Thr | Asp | Arg | Phe |
|  | 400 |  |  |  |  | 405 |  |  |  |  | 410 |  |  |  |  |

1728

| GGC | AAT | GTC | GTA | TCT | TAT | ACG | ACA | ACA | ATT | GAA | CAG | CTG | TTC | GGT | TCC |
|---|---|---|---|---|---|---|---|---|---|---|---|---|---|---|---|
| Gly | Asn | Val | Vla | Ser | Tyr | Thr | Thr | Thr | Ile | Glu | Gln | Leu | Phe | Gly | Ser |
| 415 |  |  |  |  | 420 |  |  |  | 425 |  |  |  |  |  | 430 |

1776

| GGC | ATT | ATG | GTT | CCC | GGA | TAC | GGC | GTT | GTG | CTG | AAT | AAT | GAG | TTA | ACA |
|---|---|---|---|---|---|---|---|---|---|---|---|---|---|---|---|
| Gly | Ile | Met | Val | Pro | Gly | Tyr | Gly | Val | Val | Leu | Asn | Asn | Glu | Leu | Thr |
|  |  |  |  | 435 |  |  |  |  | 440 |  |  |  |  | 445 |  |

1824

| GAC | TTC | GAT | GCG | GTG | CCT | GGC | GGC | GCA | AAT | GAA | GTG | CAG | CCG | AAT | AAA |
|---|---|---|---|---|---|---|---|---|---|---|---|---|---|---|---|
| Asp | Phe | Asp | Ala | Val | Pro | Gly | Gly | Ala | Asn | Glu | Val | Gln | Pro | Asn | Lys |
|  |  |  | 450 |  |  |  |  | 455 |  |  |  |  | 460 |  |  |

1872

| CGT | CCG | CTC | AGC | AGC | ATG | ACT | CCG | ACT | ATT | TTA | TTC | AAA | AAT | AAC | GAA |
|---|---|---|---|---|---|---|---|---|---|---|---|---|---|---|---|
| Arg | Pro | Leu | Ser | SEr | Met | Thr | Pro | Thr | Ile | Leu | Phe | Lys | Asn | Asn | Glu |
|  |  | 465 |  |  |  |  | 470 |  |  |  |  | 475 |  |  |  |

1920

| CCT | GTC | CTG | ACT | GTC | GGC | TCC | CCC | GGC | GGA | GCA | ACG | ATT | ATT | TCT | TCC |
|---|---|---|---|---|---|---|---|---|---|---|---|---|---|---|---|
| Pro | Val | Leu | Thr | Val | Gly | Ser | Pro | Gly | Gly | Ala | Thr | Ile | Ile | Ser | Ser |
|  | 480 |  |  |  |  |  | 485 |  |  |  | 490 |  |  |  |  |

1968

| GTC | CTG | CAA | ACG | ATC | CTG | AAC | AAA | GTT | GAG | TAC | GGC | ATG | GAT | CTG | AAA |
|---|---|---|---|---|---|---|---|---|---|---|---|---|---|---|---|
| Val | Leu | Gln | Thr | Ile | Leu | Asn | Lys | Val | Glu | Tyr | Gly | Met | Asp | Leu | Lys |
| 495 |  |  |  |  | 500 |  |  |  |  | 505 |  |  |  |  | 510 |

2016

| GCG | GCA | GTC | GAA | GAG | CCG | AGA | ATT | TAC | ACA | AAC | AGC | ATG | ACA | TCC | TAT |
|---|---|---|---|---|---|---|---|---|---|---|---|---|---|---|---|
| Ala | Ala | Val | Glu | Glu | Pro | Arg | Ile | Tyr | Thr | Asn | Ser | Met | Thr | Ser | Tyr |
|  |  |  |  | 515 |  |  |  |  | 520 |  |  |  |  | 525 |  |

2064

| CGA | TAT | GAA | AAA | GGA | GTG | CCG | GAA | GAA | GCC | CGC | ACA | AAA | CTG | AAC | GAA |
|---|---|---|---|---|---|---|---|---|---|---|---|---|---|---|---|
| Arg | Tyr | Glu | Lys | Gly | Val | Pro | Glu | Glu | Ala | Arg | Thr | Lys | Leu | Asn | Glu |
|  |  |  | 530 |  |  |  |  | 535 |  |  |  |  | 540 |  |  |

2112

| ATG | GGG | CAT | AAA | TTC | GGC | AGC | AGC | CCG | GTT | GAT | ATC | GGT | AAT | GTG | CAA |
|---|---|---|---|---|---|---|---|---|---|---|---|---|---|---|---|
| Met | Gly | His | Lys | Phe | Gly | Ser | Ser | Pro | Val | Asp | Ile | Gly | Asn | Val | Gln |
|  |  | 545 |  |  |  |  | 550 |  |  |  |  | 555 |  |  |  |

2160

| AGC | ATC | CTG | ATC | GAC | CGT | GAA | AAC | GGC | ACC | TTC | ACC | GGA | GTC | GCC | GAC |
|---|---|---|---|---|---|---|---|---|---|---|---|---|---|---|---|
| Ser | Ile | Leu | Ile | Asp | Arg | Glu | Asn | Gly | Thr | Phe | Thr | Gly | Val | Ala | Asp |
|  | 560 |  |  |  |  | 565 |  |  |  |  | 570 |  |  |  |  |

2208

| TCA | AGC | CGA | AAC | GGA | GCC | GCA | ATC | GGC | GTA | AAC | TTG | AAA | AAT | TAT | AAA |
|---|---|---|---|---|---|---|---|---|---|---|---|---|---|---|---|
| Ser | Ser | Arg | Asn | Gly | Ala | Ala | Ile | Gly | Val | Asn | Leu | Lys | Asn | Tyr | Lys |
| 575 |  |  |  |  | 580 |  |  |  |  | 585 |  |  |  |  | 590 |

2256

AAA TAACAAGACA AAAAGCCTCG TTTCTCAAGC TGAGAAATGA GGCTTTTGTT  2309
Lys

TATTCTGCAC TGTATTCAGA TGAGGTTTTT TCAGACGTTA ATGATGCAAG CGAAAGCACA  2369

CCGCACATCG CGA  2382

(2) INFORMATION FOR SEQ ID NO:3:
    (i) SEQUENCE CHARACTERISTICS:
        (A) LENGTH: 13 amino acids
        (B) TYPE: amino acid
        (D) TOPOLOGY: linear
    (ii) MOLECULE TYPE: peptide
    (xi) SEQUENCE DESCRIPTION: SEQ ID NO:3:

Ala Gly Asp Pro Trp Ala Tyr Gln Glu Gly Ser Ala Asn
1              5                  10

(2) INFORMATION FOR SEQ ID NO:4:
    (i) SEQUENCE CHARACTERISTICS:
        (A) LENGTH: 17 base pairs
        (B) TYPE: nucleic acid
        (C) STRANDEDNESS: single
        (D) TOPOLOGY: linear
    (ii) MOLECULE TYPE: DNA (genomic)
    (xi) SEQUENCE DESCRIPTION: SEQ ID NO:4:

TGGGCNTAYC ARGARGG  17

(2) INFORMATION FOR SEQ ID NO:5:

-continued (i) SEQUENCE CHARACTERISTICS:
    (A) LENGTH: 8 amino acids
    (B) TYPE: amino acid
    (C) STRANDEDNESS: unknown
    (D) TOPOLOGY: linear
(ii) MOLECULE TYPE: peptide
(xi) SEQUENCE DESCRIPTION: SEQ ID NO:5:

Val Glu Tyr Gly Met Asp Leu Lys
1               5

(2) INFORMATION FOR SEQ ID NO:6:
    (i) SEQUENCE CHARACTERISTICS:
        (A) LENGTH: 17 base pairs
        (B) TYPE: nucleic acid
        (C) STRANDEDNESS: single
        (D) TOPOLOGY: linear
    (ii) MOLECULE TYPE: DNA (genomic)
    (xi) SEQUENCE DESCRIPTION: SEQ ID NO:6:

GARTAYGGNA  TGGAYYT                                             17

(2) INFORMATION FOR SEQ ID NO:7:
    (i) SEQUENCE CHARACTERISTICS:
        (A) LENGTH: 17 base pairs
        (B) TYPE: nucleic acid
        (C) STRANDEDNESS: single
        (D) TOPOLOGY: linear
    (ii) MOLECULE TYPE: DNA (genomic)
    (xi) SEQUENCE DESCRIPTION: SEQ ID NO:7:

ARRTCCATNC  CRTAYTC                                             17

(2) INFORMATION FOR SEQ ID NO:8:
    (i) SEQUENCE CHARACTERISTICS:
        (A) LENGTH: 27 base pairs
        (B) TYPE: nucleic acid
        (C) STRANDEDNESS: double
        (D) TOPOLOGY: linear
    (ii) MOLECULE TYPE: DNA (genomic)
    (xi) SEQUENCE DESCRIPTION: SEQ ID NO:8:

CTAGAGGATC  CCCGGGTACC  GAGCTCG                                 27

(2) INFORMATION FOR SEQ ID NO:9:
    (i) SEQUENCE CHARACTERISTICS:
        (A) LENGTH: 37 base pairs
        (B) TYPE: nucleic acid
        (C) STRANDEDNESS: single
        (D) TOPOLOGY: linear
    (ii) MOLECULE TYPE: DNA (genomic)
    (xi) SEQUENCE DESCRIPTION: SEQ ID NO:9:

AAAAGCCTGC  TTTCTCAAGC  TGAGAAATGA  GGCTTTT                     37